(12) United States Patent
Friedrichs

(10) Patent No.: US 9,795,457 B2
(45) Date of Patent: Oct. 24, 2017

(54) DENTAL DRILL AND METHOD FOR PRODUCING SAME

(76) Inventor: Arno Friedrichs, Kulmbach (DE)

( * ) Notice: Subject to any disclaimer, the term of this patent is extended or adjusted under 35 U.S.C. 154(b) by 382 days.

(21) Appl. No.: 13/979,718

(22) PCT Filed: Jan. 20, 2012

(86) PCT No.: PCT/EP2012/050852
§ 371 (c)(1),
(2), (4) Date: Jul. 15, 2013

(87) PCT Pub. No.: WO2012/101050
PCT Pub. Date: Aug. 2, 2012

(65) Prior Publication Data
US 2013/0302748 A1    Nov. 14, 2013

(30) Foreign Application Priority Data

Jan. 27, 2011   (DE) .................. 10 2011 000 352

(51) Int. Cl.
| | |
|---|---|
| B23B 51/00 | (2006.01) |
| A61C 1/05 | (2006.01) |
| A61C 3/02 | (2006.01) |
| B23B 51/06 | (2006.01) |
| B23P 15/32 | (2006.01) |

(52) U.S. Cl.
CPC .............. A61C 1/055 (2013.01); A61C 3/02 (2013.01); B23B 51/06 (2013.01); B23P 15/32 (2013.01); *B22F 2998/00* (2013.01)

(58) Field of Classification Search
CPC ......... A61C 3/02; A61C 8/0089; A61C 5/023; A61C 1/055; B23B 51/042; B23B 51/0453; B23B 51/0486; B23B 51/06; B22F 2998/00

USPC .............. 433/81–87, 165, 166; 408/224, 230
See application file for complete search history.

(56) References Cited

U.S. PATENT DOCUMENTS

| | | | |
|---|---|---|---|
| 2,541,849 A | * | 2/1951 | Villeneuve .................. 76/108.6 |
| 3,073,189 A | | 1/1963 | Paige |
| 3,842,632 A | * | 10/1974 | Nelson .......................... 433/165 |
| 4,021,920 A | * | 5/1977 | Kirschner et al. .............. 433/82 |
| 4,704,055 A | | 11/1987 | Guehring |
| 5,575,650 A | | 11/1996 | Niznick et al. |

(Continued)

FOREIGN PATENT DOCUMENTS

| | | |
|---|---|---|
| CN | 1575913 A | 2/2005 |
| CN | 101636364 A | 1/2010 |

(Continued)

OTHER PUBLICATIONS

International Search Report of PCT/EP2012/050852, dated May 18, 2012.

*Primary Examiner* — Yogesh Patel
(74) *Attorney, Agent, or Firm* — Collard & Roe, P.C.

(57) ABSTRACT

The invention relates to a method for producing a dental drill that has a shank (1) and a work section. The shank contains a centrally arranged, continuous first channel (3). The work section contains one or more continuous, spiral-shaped further channels (4a, 4b). The first channel and the further channels open into a common chamber (5) connecting the shank and the work section. The shank is sintered with the work section in order to form a one-piece, sintered component that encloses the chamber connecting the shank and the work section.

5 Claims, 2 Drawing Sheets

(56) References Cited

U.S. PATENT DOCUMENTS

| | | | |
|---|---|---|---|
| 6,045,301 A * | 4/2000 | Kammermeier | B23B 51/06 408/230 |
| 6,210,083 B1 * | 4/2001 | Kammermeier | B23B 51/06 279/20 |
| 7,340,978 B2 | 3/2008 | Kugelberg et al. | |
| 8,091,459 B2 | 1/2012 | Kugelberg et al. | |
| 8,501,082 B2 | 8/2013 | Hock et al. | |
| 2005/0084351 A1 | 4/2005 | Friedrichs | |
| 2008/0080938 A1 | 4/2008 | Makino et al. | |
| 2010/0150673 A1 * | 6/2010 | Schneider et al. | 408/59 |
| 2011/0182684 A1 | 7/2011 | Yoon et al. | |

FOREIGN PATENT DOCUMENTS

| | | |
|---|---|---|
| DE | 74 35 411 U | 2/1976 |
| DE | 32 08 282 A1 | 10/1982 |
| DE | 36 36 798 A1 | 4/1988 |
| DE | 10 2009 043 875 A1 | 3/2011 |
| EP | 0 118 035 A1 | 9/1984 |
| JP | 2005-501743 A | 1/2005 |
| SU | 722 699 A1 | 3/1980 |
| SU | 1 046 039 A1 | 10/1983 |
| WO | WO 2010/005193 A2 | 1/2010 |

\* cited by examiner

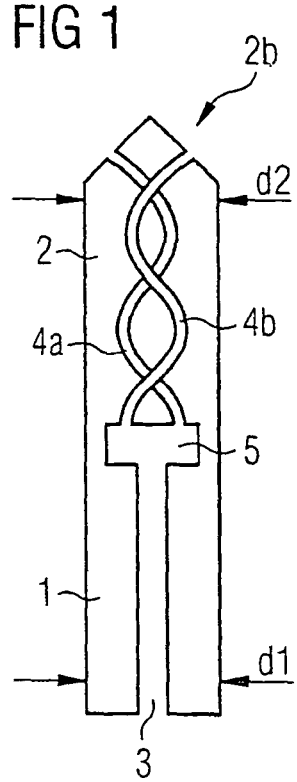
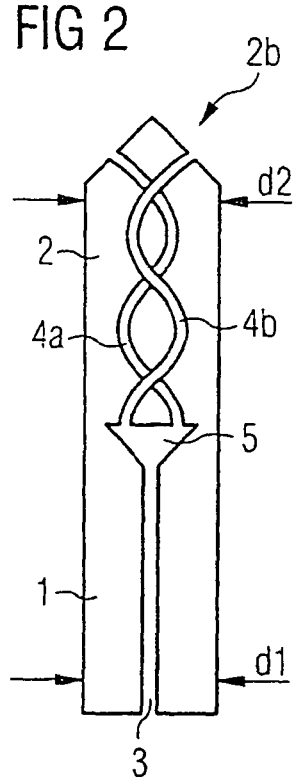

DENTAL DRILL AND METHOD FOR PRODUCING SAME

CROSS REFERENCE TO RELATED APPLICATIONS

This application is the National Stage of PCT/EP2012/050852 filed on Jan. 20, 2012, which claims priority under 35 U.S.C. §119 of German Application No. 10 2011 000 352.5 filed on Jan. 27, 2011, the disclosures of which are incorporated by reference. The international application under PCT article 21(2) was not published in English.

BACKGROUND OF THE INVENTION

1. Field of the Invention

The invention relates to a dental drill and a method for production thereof.

2. The Prior Art

Dental drills of one-piece construction are already known, which include a shank and an adjoining work section having one or more cutting edges, the drill being furnished in the interior of the shank with a central coolant channel. This coolant channel serves, in working operation of the dental drill, for the purpose of transporting a coolant, particularly a cooling liquid, into the region of the work section where it is used for cooling the work section and the currently treated tooth of a patient.

In known dental drills of that kind the said coolant channel opens into the transition region between the shank and the work section so that coolant already issues in the region of the rear end of the work section and thus directly cools merely the rear part of the work section. A disadvantage of drills of that kind is that only inadequate cooling of the cutting region of the dental drill and also inadequate cooling of the currently treated tooth of the patient take place.

A dental drill having a shank and a work section connected with the shank is described in DE 10 2009 043 875.0. The shank includes a centrally arranged, continuous first channel. The work section has one or more continuous, helically extending further channels. Provided between the shank and the work section is a gap into which the first channel and the further channels open. The shank and the work section are connected together by means of clamping sleeve, a soldered connection or an adhesive connection.

SUMMARY OF THE INVENTION

The object of the invention consists in indicating a method of producing a dental drill and a dental drill with improved cooling of the cutting region, which drill does not require any additional connecting material in the transition region between the shank and the work section, particularly any clamping sleeve, solder material or also adhesive material.

This object is fulfilled by a method with the features according to one aspect of the invention or by a dental drill with the features according to another aspect of the invention. Advantageous embodiments and developments of the invention are discussed below.

The advantages of the invention consist particularly in that a dental drill is provided which in the transition region between the shank and work section has no visible seam location or joint location. Moreover, no connecting materials are provided in this transition region, such as, for example, solder material, adhesive material or a clamping sleeve. This has the advantage that the bio-compatibility of the dental drill is improved. In this connection it is of significance that a dental drill during tooth treatment has contact with the lips, tongue and teeth of a patient. Due to the non-presence of connecting materials such as a clamping sleeve, solder material or adhesive material it is ensured that no materials harmful to the human organism can be absorbed by way of the mucous membrane of the patient and thereby place the health of the patient at risk. Moreover, in advantageous manner patients who have allergies to the material of the clamping sleeve, solder connection or adhesive connection can be prevented from coming into contact with these materials.

A further advantage of the invention is that creation of sealing problems in the transition region between the shank and the work section is excluded. This is attributable to the fact that through the sintering of the shank with the work section the particles present in the surface region of the shank mix with the particles present in the surface region of the work of the work section in such a manner that a joint-free connection of the shank with the work section arises. Consequently, there are no visible seam locations or joint locations through which cooling liquid could undesirably escape during operation of the dental drill.

Moreover, in the case of a dental drill according to the invention it is ensured that the cooling liquid is guided without pressure loss up to the end region, which is remote from the shank, of the helically extending further channels and issues at that point so that the cutting region of the dental drill and also the treated tooth of the patient are cooled in desired manner.

BRIEF DESCRIPTION OF THE DRAWINGS

Further advantageous characteristics of the invention are evident from the exemplifying explanation thereof by way of the figures, in which:

FIG. 1 shows a longitudinal sectional illustration of a dental drill according to a first embodiment of the invention, FIG. 2 shows a longitudinal sectional illustration of a dental drill according to a second embodiment of the invention.

DETAILED DESCRIPTION OF THE PREFERRED EMBODIMENTS

Figure 3A:
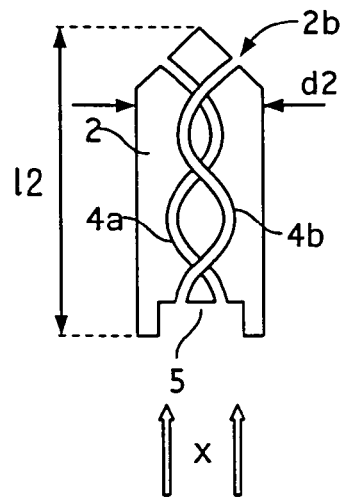
FIGS. 3A, 3B, 3C, and 3D show diagrams for explanation of a method of producing a dental drill according to the invention

Dental drills according to the invention have a shank and a work section, wherein the shank has a centrally arranged, continuous first channel, the work section has one or more continuous, helically extending further channels, the first channel and the further channels open into a common chamber connecting the shank and the work section and the shank and the work section are sintered together. A design of that kind of a dental drill creates the possibility of transporting, during working operation of the dental drill, a sufficient quantity of coolant, particularly cooling liquid, directly to the cutting region of the work section of the dental drill so that cooling, which is improved by comparison with known dental drills, of the cutting region and the currently treated tooth of the patient is achieved.

FIG. 1 shows a diagram of a longitudinal sectional illustration of a dental drill according to a first embodiment of the invention. This dental drill has a cylindrically formed shank 1 and a similarly cylindrically formed work section 2. A continuous first channel 3 extending in axial direction is centrally provided in the shank 1. The diameter of the shank 1 is denoted by d1.

Provided in the work section 2 of the dental drill are two continuous, helically extending further channels 4a and 4b which communicate with the cutting region 2b of the work section 2. The diameter of the work section 2 is denoted by d2 and corresponds with the diameter d1 of the shank 1.

A chamber 5 is provided in the interior of the dental drill in the transition region from shank 1 to work section 2. In the case of the embodiment shown in FIG. 1 this chamber 5 is of disc-shaped construction. Not only the first channel 3, but also the two helical further channels 4a and 4b open into the chamber 5, which can alternatively also be constructed to be slot-shaped, cylindrical, polygonal or conical.

In working operation of the dental drill, for example for the preparation of a jawbone for later reception of an implant or for removal of caries from a tooth of a patient a coolant, particularly a cooling liquid, is delivered under low pressure into the first channel 3 from the bottom in FIG. 1. The coolant runs through the rectilinearly formed first channel 3, fills the chamber 5 provided in the transition region from the shank 1 to the work section 2, penetrates from the chamber 5 into the helically extending further channels 4a and 4b, runs through these and is then delivered in the cutting region 2b of the work section 2. Consequently, not only the cutting region forming the work region of the dental drill, but also the currently treated tooth of the patient are directly cooled by the coolant issuing from the channels 4a and 4b.

The shank 1 and the work section 2 of the dental drill can consist of the same material or of different materials. The shank 1 preferably consists of steel, ceramic, hard metal or plastic and the work section 2 of steel, ceramic or hard metal. The cutting region 2b of the work section 2 can consist of the same material as the remaining part of the work section 2 or also of another material.

FIG. 2 shows a diagram of a longitudinal sectional illustration of a dental drill according to a second embodiment of the invention. This dental drill has a cylindrically formed shank 1 and a similarly cylindrically formed work section 2. A continuous first channel 3 extending in axial direction is centrally provided in the shank 1. The diameter of the shank 1 is denoted by d1.

Provided in the work section 2 of the dental drill are two continuous, helically extending further channels 4a and 4b communicating with the cutting region 2b of the work section 2. The diameter of the work region 2 is denoted by 2 and corresponds with the diameter d1 of the shank 1.

A chamber 5 is provided in the interior of the dental drill in the transition region from the shank 1 to the work section 2. In the case of the embodiment shown in FIG. 2 this chamber 5 is constructed to be conical, but can also have a different shape. Not only the first channel 3, but also the two helical further channels 4a and 4b open into the chamber 5. In the illustrated embodiment the chamber 5 is provided in the shank 1. Alternatively thereto it can also be provided in the work section 2. A further alternative consists in providing a part of the chamber in the shank 1 and the other part of the chamber in the work section 2.

In working operation of the dental drill, for example for removal of caries from a tooth of a patient, a coolant, particularly a cooling liquid, is introduced under pressure into the first channel 3 from the bottom in FIG. 2. The coolant runs through the rectilinearly formed first channel 3, fills the chamber 5 provided between the shank 1 and the work section 2, penetrates from the chamber 5 into the helically extending further channels 4a and 4b, runs through these and is then issued in the cutting region 2b of the work section 2. Consequently, not only the cutting region, which forms the work region of the dental drill, but also the currently treated tooth of the patient are directly cooled by the coolant issuing from the channels 4a and 4b.

The shank 1 and the work section 2 of the dental drill can consist of the same material or of different materials. Preferably, the shank 1 consists of steel, ceramic, hard metal or plastic and the work section 2 of steel, ceramic or hard metal. The cutting region 2b of the work section 2 can consist of the same material as the remaining part of the work section 2 or also of a different material.

FIGS. 3A to 3D shows diagrams for explanation of a method of producing a dental drill according to the invention. In that case, production of the dental drill shown in FIG. 1 is explained on the basis of FIGS. 3A and 3B and production of the dental drill shown in FIG. 2 is explained on the basis of FIGS. 3C and 3D.

For production of the dental drill shown in FIG. 1 initially a shank 1 and a work section 2 are produced independently of one another. The shank 1 is shown in FIG. 3B. The work section 2 is illustrated in FIG. 3A.

For production of the shank 1, plastic material is extruded by a first extrusion tool in such a manner that a first body, which consists of plastic material, with a centrally arranged, continuous first channel issues from the first extrusion tool. The first body issued from the first extrusion tool is of cylindrical construction and has a diameter d1. The body issued from the first extrusion tool is cut to a predetermined length l1 and then dried so that its consistency solidifies.

For production of the work section 2, plastic material is extruded by a second extrusion tool in such a manner that a second body, which consists of plastic material, with rectilinearly extending further channels issues from the second extrusion tool. The body issued from the second extrusion tool is similarly of cylindrical construction. It has a diameter d2 which corresponds with the diameter d1 of the shank. The second body issued from the second extrusion tool is cut to a predetermined second length l2. The cut-to-length second body is subjected to a uniform twisting of a rolling motion, the speed of which constantly changes over the entire length l2, by means of a friction surface arrangement while being supported over its entire length. Helically extending further channels 4a and 4b, as illustrated in FIG. 3A, are thereby formed from the initially rectilinearly extending further channels. The body produced in this manner is dried so that its consistency solidifies. The chamber 5, which in the illustrated embodiment is of rectangular form, is ground into the rear region of the dried body. The cutting region 2b is similarly formed in the front region of the dried body by means of a grinding process.

Figure 3C:
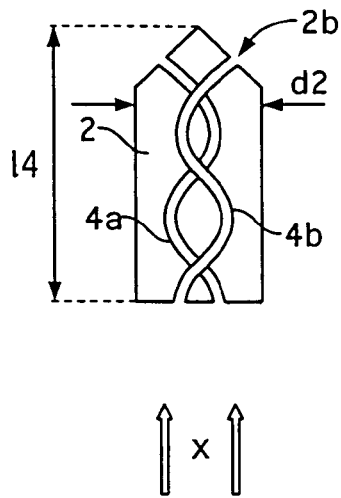
Figure 3B:
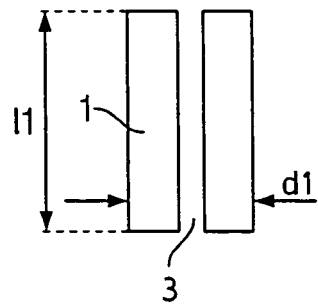

Thereafter—as is illustrated between FIGS. 3A and 3B by the arrows x—the bodies solidified by drying are placed against one another in axial direction and heated. This heating is carried out in such a manner that the mutually adjoining surfaces of the heated bodies melt and that the mutually adjoining surfaces are sintered together in such a manner that after connection thereof no seam locations or joint locations are visible. The sintered-together bodies are subsequently dried again so that the consistency thereof further solidifies.

A one-piece sintered component, which completely encloses the chamber 5 connecting the shank 1 and the work section 2, is formed by the afore-described sintering of the shank to the work section. Consequently, the transition region between the shank and the work section is free of additional connecting materials of any kind.

Figure 3D:
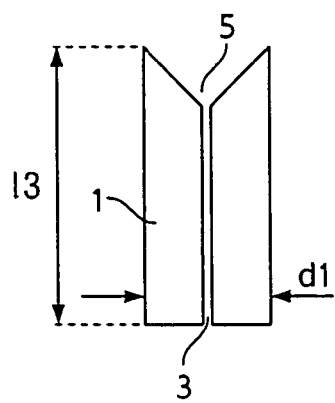

For producing the dental drill shown in FIG. 2 initially a shank 1 and a work section 2 are produced independently of one another. The shank 1 is shown in FIG. 3D. The work section 2 is illustrated in FIG. 3C.

For production of the shank 1, plastic material is extruded by a first extrusion tool in such a manner that a first body, which consists of plastic material, with a centrally arranged, continuous first channel 3 issues from the first extrusion tool. The first body issued from the first extrusion tool is of cylindrical construction and has a diameter d1. The body issued from the first extrusion tool is cut to a predetermined length l3 and then dried so that the consistency thereof solidifies. The chamber 5, which in the illustrated embodiment is of conical construction, is ground into the front region of the dried body.

For production of the work section 2, plastic material is extruded by a second extrusion tool in such a manner that a second body, which consists of plastic material, with rectilinearly extending further channels issues from the second extrusion tool. The body issued from the second extrusion tool is similarly of cylindrical construction. It has a diameter d2, which corresponds with the diameter d1 of the shank. The second body issued from the second extrusion tool is cut to a predetermined second length l4. The cut-to-length second body is subjected to a uniform twisting of a rolling motion, the speed of which constantly changes over the entire length l4, by means of a friction surface arrangement while being supported over its entire length. Helically extending further channels 4a and 4b, as illustrated in FIG. 3C, are thereby formed from the initially rectilinearly extending further channels. The body produced in this manner is dried so that the consistency thereof solidifies. The cutting region 2b is formed in the front region of the dried body by means of a grinding process.

Thereafter—as illustrated between the FIGS. 3D and 3C by the arrows x—the bodies solidified by drying are placed against one another in axial direction and heated. This heating is carried out in such a manner that the mutually adjoining surfaces of the heated bodies melt and that the mutually adjoining surfaces are sintered together in such a manner that after connection thereof no seam locations or joint locations are visible. The bodies sintered together are subsequently dried again so that the consistency thereof further solidifies.

A one-piece sintered component, which completely encloses the chamber 5 connecting the shank 1 and the work section 2, is formed by the afore-described sintering of the shank to the work section. Consequently, the transition region between the shank and the work section is free of additional connecting materials of any kind.

Figures 4A, 4B:
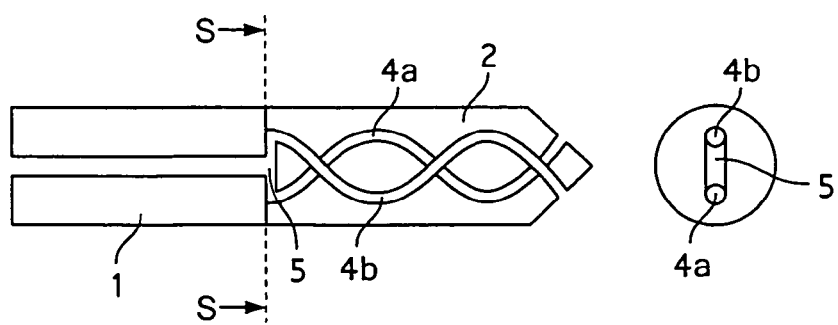
FIGS. 4A and 4B show a longitudinal sectional illustration of a dental drill according to a third embodiment of the invention.

FIG. 4A shows a longitudinal sectional illustration of a dental drill according to a third embodiment of the invention. In this third embodiment the chamber 5 provided in the transition region from the shank 1 to the work section 2 is of slot-shaped construction. The width of the chamber 5 in the radial direction of the dental drill is matched to the radial external dimensions of the helically extending channels 4a and 4b so that the chamber 5 does not protrude in radial direction outwardly beyond the helically extending channels. This is also apparent from the illustration on the righthand side of FIG. 4B, wherein this illustration shows a cross-sectional illustration of the dental drill along the section line S shown by a dot-dashed line on the lefthand side of FIG. 4A.

In the case of the afore-described embodiments the shank in each instance has a centrally arranged central channel. According to a modified form of embodiment a dental drill can also be constructed in such a manner that the helically extending channels provided in the work region extend as far as the shank and also run completely through the shank. In this case the feed of coolant is provided into the grip member, which is not illustrated in the figures, of the dental drill.

A chamber can, by way of example, similarly be provided there, through which chamber the cooling liquid supplied from a cooling liquid source is conducted onward in the helically extending channels of the dental drill.

The chamber 5 is in radial direction of the drill broader than the first continuous channel 3 in shank 1. Also end regions of the further channels 4a, 4b opening into chamber 5 are still helically twisted.

REFERENCE NUMERAL LIST 1 shank
2 work section
2b cutting region of the work section
3 first channel
4a, 4b further channels
5 chamber
d1 diameter of the shank
d2 diameter of the work section
l1, l3 length of the shank
l2, l4 length of the work section

The invention claimed is:

1. Dental drill with a shank (1) and a work section (2), wherein the shank has a centrally arranged, continuous first channel (3), the work section has more than one internal continuous, helically extending further channels (4a, 4b), a chamber (5) is provided between the shank and work section, the first channel and the further channels open into the chamber and the shank and the work section form a one-piece component which is connected by sintering and which completely encloses the chamber (5) connecting the shank (1) and the work section (2), wherein the transition region between the shank and the work section is free of additional connection materials, wherein the transition region between the shank and the work section has no visible seam locations or joint locations and wherein the chamber is disc-shaped; and the chamber (5) is in radial direction of the drill broader than the first continuous channel (3) in shank (1); and
end regions of the further channels (4a, 4b) opening into chamber (5) are still helically twisted.

2. Dental drill with a shank (1) and a work section (2), wherein the shank has a centrally arranged, continuous first channel (3), the work section has more than one internal continuous, helically extending further channels (4a, 4b), a chamber (5) is provided between the shank and work section, the first channel and the further channels open into the chamber and the shank and the work section form a one-piece component which is connected by sintering and which completely encloses the chamber (5) connecting the shank (1) and the work section (2), wherein the transition region between the shank and the work section is free of additional connection materials, wherein the transition region between the shank and the work section has no visible seam locations or joint locations and wherein the chamber (5) is slot-shaped; and the chamber (5) is in radial direction of the drill broader than the first continuous channel (3) in shank (1); and
end regions of the further channels (4a, 4b) opening into chamber (5) are still helically twisted.

3. Dental drill with a shank (1) and a work section (2), wherein the shank has a centrally arranged, continuous first channel (3), the work section has more than one internal continuous, helically extending further channels (4a, 4b), a chamber (5) is provided between the shank and work section, the first channel and the further channels open into the chamber and the shank and the work section form a one-piece component which is connected by sintering and which completely encloses the chamber (5) connecting the shank (1) and the work section (2), wherein the transition region between the shank and the work section is free of additional connection materials, wherein the transition region between the shank and the work section has no visible seam locations or joint locations and wherein the chamber (5) is polygonal; and the chamber (5) is in radial direction of the drill broader than the first continuous channel (3) in shank (1); and
end regions of the further channels (4a, 4b) opening into chamber (5) are still helically twisted.

4. Dental drill with a shank (1) and a work section (2), wherein the shank has a centrally arranged, continuous first channel (3), the work section has more than one internal continuous, helically extending further channels (4a, 4b), a chamber (5) is provided between the shank and work section, the first channel and the further channels open into the chamber and the shank and the work section form a one-piece component which is connected by sintering and which completely encloses the chamber (5) connecting the shank (1) and the work section (2), wherein the transition region between the shank and the work section is free of additional connection materials, wherein the transition region between the shank and the work section has no visible seam locations or joint locations and wherein the chamber (5) is conical; and the chamber (5) is in radial direction of the drill broader than the first continuous channel (3) in shank (1); and
end regions of the further channels (4a, 4b) opening into chamber (5) are still helically twisted.

5. Dental drill with a shank (1) and a work section (2), wherein the shank has a centrally arranged, continuous first channel (3), the work section has more than one internal continuous, helically extending further channels (4a, 4b), a chamber (5) is provided between the shank and work section, the first channel and the further channels open into the chamber and the shank and the work section form a one-piece component which is connected by sintering and which completely encloses the chamber (5) connecting the shank (1) and the work section (2), wherein the transition region between the shank and the work section is free of additional connection materials, wherein the transition region between the shank and the work section has no visible seam locations or joint locations and wherein the chamber (5) is cylindrical; and the chamber (5) is in radial direction of the drill broader than the first continuous channel (3) in shank (1); and
end regions of the further channels (4a, 4b) opening into chamber (5) are still helically twisted.

* * * * *